United States Patent
Iwa et al.

(10) Patent No.: US 7,524,062 B2
(45) Date of Patent: Apr. 28, 2009

(54) OPHTHALMOLOGIC APPARATUS

(75) Inventors: Yoichiro Iwa, Tokyo (JP); Gaku Takeuchi, Tokyo (JP); Takao Tanabe, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 0 days.

(21) Appl. No.: 12/003,011

(22) Filed: Dec. 19, 2007

(65) Prior Publication Data

US 2008/0151189 A1 Jun. 26, 2008

(30) Foreign Application Priority Data

Dec. 22, 2006 (JP) ............... 2006-345627

(51) Int. Cl.
*A61B 3/14* (2006.01)
(52) U.S. Cl. .................................... 351/206
(58) Field of Classification Search ............... 351/206, 351/205, 221, 214, 246
See application file for complete search history.

(56) References Cited

U.S. PATENT DOCUMENTS

| | | | |
|---|---|---|---|
| 4,773,749 A | * | 9/1988 | Ohtomo et al. ............ 351/206 |
| 5,090,799 A | * | 2/1992 | Makino et al. ............ 351/221 |
| 5,943,115 A | | 8/1999 | Ferguson |
| 6,273,566 B1 | | 8/2001 | Kobayashi |
| 2004/0252276 A1 | | 12/2004 | Nanjo et al. |
| 2006/0077346 A1 | | 4/2006 | Matsumoto |

FOREIGN PATENT DOCUMENTS

| | | |
|---|---|---|
| EP | 0 697 611 A2 | 2/1996 |
| WO | WO 01/28408 A2 | 4/2001 |

\* cited by examiner

*Primary Examiner*—Hung X Dang
(74) *Attorney, Agent, or Firm*—Dickstein Shapiro LLP (57) ABSTRACT

The invention is directed to an ophthalmologic apparatus. The apparatus includes a photographing system that illuminates an ocular fundus of a tested eye, and photographs an image of the ocular fundus of the tested eye based on a reflective beam from the ocular fundus, an aberration measurement part for measuring an optical aberration of the tested eye, an aberration compensation device disposed in the photographing system for compensating the aberration of the tested eye based on signals from the aberration measurement part, and a focusing device for substantially focusing corresponding to a refractive power of the tested eye by moving a part of an optical system comprising the photographing system along an optical axis direction.

4 Claims, 5 Drawing Sheets

OPHTHALMOLOGIC APPARATUS

PRIORITY CLAIM

This application claims priority from Japanese Patent Application No. 2006-345627, filed with the Japanese Patent Office on Dec. 22, 2006, the contents of which are incorporated herein by reference in their entirety.

BACKGROUND OF THE INVENTION

1. Field of the Invention

The present invention is related to an opthalmologic apparatus that illuminates an ocular fundus of a tested eye, and can photograph the ocular fundus of the tested eye with high resolution based on the reflective beam from the ocular fundus.

2. Description of Related Art

By convention, it is known an opthalmologic apparatus as an ocular fundus camera that illuminates an ocular fundus of a tested eye, and can photograph an ocular fundus of a tested eye based on the reflective beam from the ocular fundus.

An ocular fundus camera of this kind has the disadvantages of not being able to obtain an ocular fundus image with high resolution as well as a clear image of the ocular fundus having high magnification with effects of aberration of an ocular optical system because the reflective beam of the ocular fundus passes through the ocular optical system formed by a cornea, a crystal lens, a glass body and so on.

Therefore, a technology to obtain a clear image of the ocular fundus having high magnification is proposed by providing on the image photographing system an aberration measurement part which measures an optical aberration of a tested eye and a variable shape mirror (deformable mirror) which compensates, based on the signals from the aberration measurement part, the distortions of the wave front of the reflective beam generated due to the optical aberration (refer to, for example, U.S. Pat. No. 5,943,115).

An opthalmologic apparatus of this kind, although has shallow focus depth, is able to obtain an ocular fundus image having high magnification that can determine till the photoreceptor cell level, but an ocular fundus is formed from a tissue comprising transparent multi-layers, with only an ocular fundus image focused on a region of a layer in the depth direction, it is problematic that sufficient information with regard to the ocular fundus can not be obtained. There is a need for an opthalmologic apparatus that can solve the situation.

SUMMARY OF THE INVENTION

The present invention provides an opthalmologic apparatus that satisfies the need. The present invention provides an opthalmologic apparatus that can obtain a plurality of ocular fundus images with different focused positions in the depth direction of an ocular fundus and a clear image of the ocular fundus of each tissue in the depth direction.

A first aspect of the present invention relates to an opthalmologic apparatus, including a photographing system that illuminates an ocular fundus of a tested eye, and photographs an image of the ocular fundus of the tested eye based on a reflective beam from the ocular fundus, an aberration measurement part for measuring an optical aberration of the tested eye, an aberration compensation device disposed in the photographing system for compensating the aberration of the tested eye based on signals from the aberration measurement part, and a focusing device for substantially focusing corresponding to a refractive power of the tested eye by moving a part of an optical system comprising the photographing system along an optical axis direction, wherein after performing the substantial focusing of the image of the ocular fundus by the focusing device, the focusing device is sequentially adjusted to move stepwise at a predetermined minute pitch centering on the focused position, and the image of the ocular fundus of the tested eye is photographed at each of the positions that the focusing device is sequentially adjusted to move stepwise.

Advantageously, the focusing device is a movement device for moving a lens system comprising the photographing system.

Advantageously, the focusing device is an optical path length conversion device comprising the photographing system.

A second aspect of the present invention relates to an opthalmologic apparatus, including a photographing system that illuminates an ocular fundus of a tested eye, and photographs an image of the ocular fundus of the tested eye based on a reflective beam from the ocular fundus, an aberration measurement part for measuring an optical aberration of the tested eye, an aberration compensation device disposed in the photographing system for compensating the aberration of the tested eye based on signals from the aberration measurement part, a first focusing device for substantially focusing corresponding to a refractive power of the tested eye by moving a part of an optical system comprising the photographing system along an optical axis direction, and a second focusing device which, after performing the substantial focusing of the image of the ocular fundus by the first focusing device, is sequentially adjusted to move stepwise at a predetermined minute pitch centering on the focused position, wherein each of the images of the ocular fundus of the tested eye is photographed at each of the positions in which the second focusing device is sequentially adjusted to move stepwise.

BRIEF DESCRIPTION OF THE DRAWINGS

These and other features, aspects, and advantages of the present invention will become better understood with regard to the following description, appended claims, and accompanying drawings.

DETAILED DESCRIPTION OF THE INVENTION

An embodiment of an opthalmologic apparatus according to the present invention will be described below with reference to the accompanying drawings.

Figure 1:
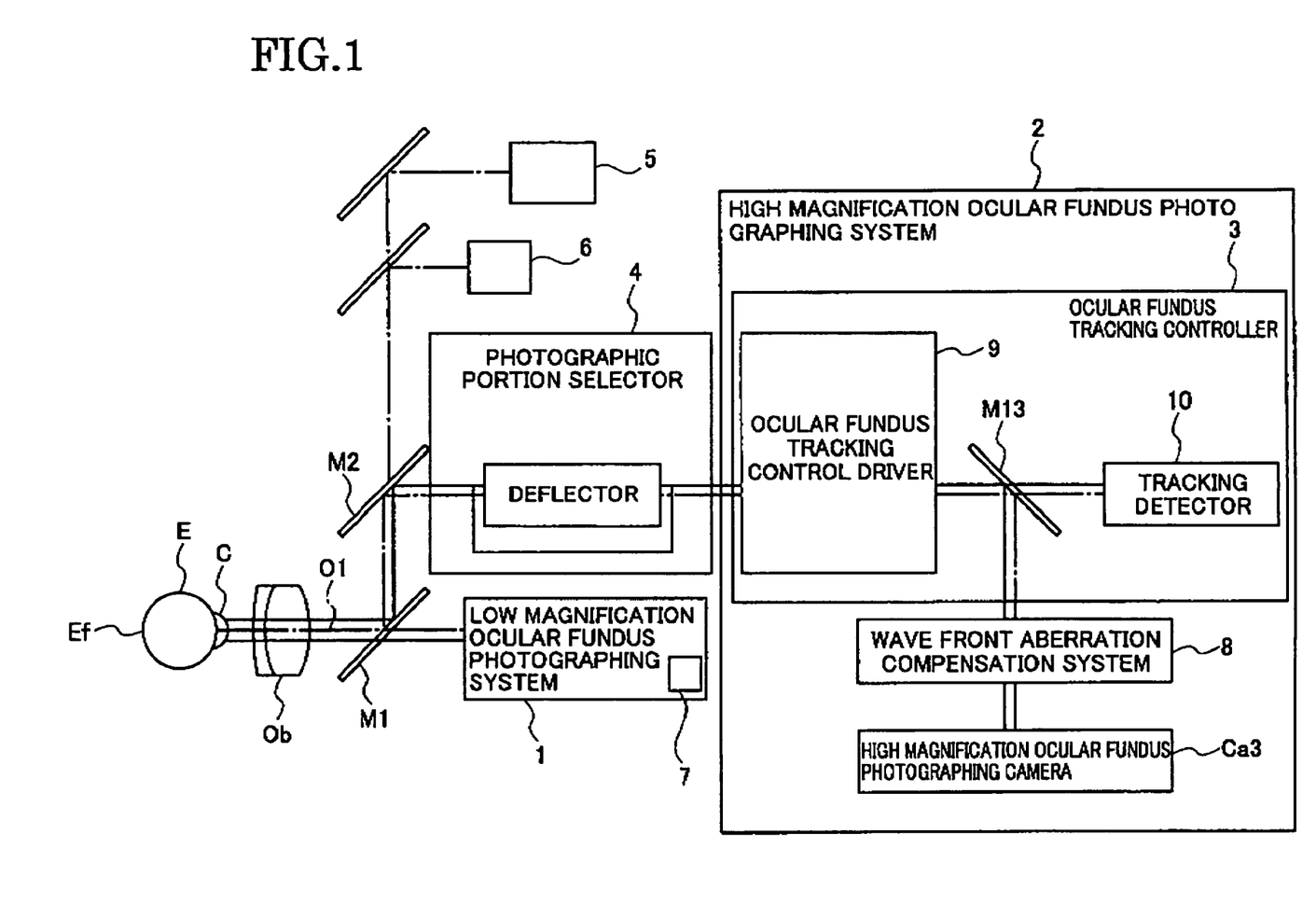
FIG. 1 is a block diagram illustrating an opthalmologic apparatus in accordance with the present invention.

FIG. 1 is a block diagram illustrating an opthalmologic apparatus according to the present invention. The opthalmologic apparatus includes a low magnification ocular fundus photographing system 1 for observing an ocular fundus Ef of a tested eye E, a high magnification ocular fundus photographing system 2 for photographing the ocular fundus Ef of the tested eye, an ocular fundus tracking controller 3 for letting the high magnification ocular fundus photographing system 2 to follow up the gaze direction of the tested eye E, and a photographing portion selector 4 for selecting a photographing portion.

Figure 2:
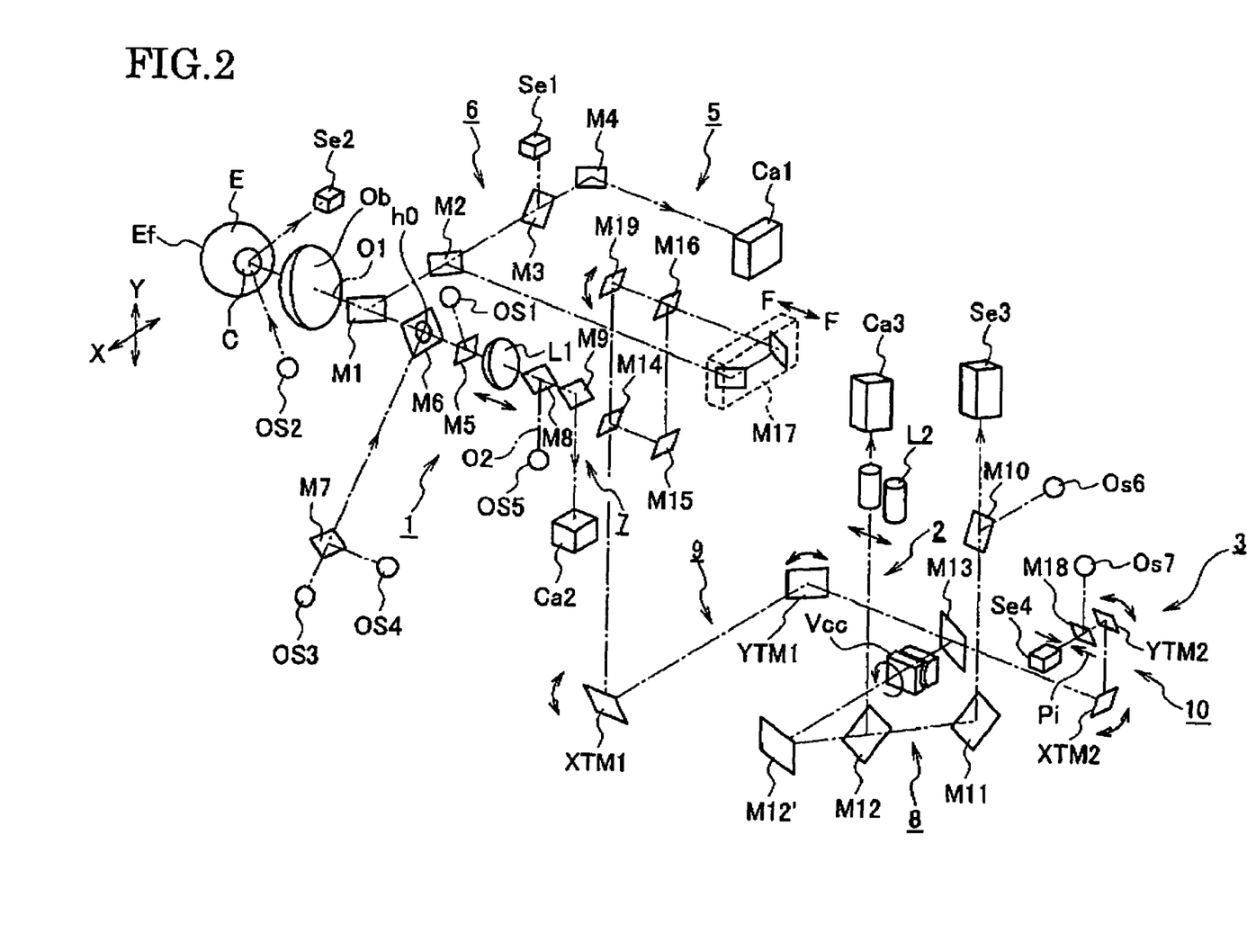
FIG. 2 is a detailed view illustrating an optical system of the opthalmologic apparatus shown in FIG. 1.

FIG. 2 is a detailed view of an optical system of the opthalmologic apparatus illustrated in FIG. 1. The optical system includes an object lens Ob positioned in front of the tested eye E, the low magnification ocular fundus photographing system 1, the high magnification ocular fundus photographing system (imaging system) 2, an anterior eye segment observation system 5, an alignment detection system 6, a fixation target projection system 7, a wave front aberration compensation system 8, an ocular fundus tracking control driver 9, and a tracking detector 10.

(Anterior Eye Segment Observation System 5)

The anterior eye segment observation system 5 includes an anterior eye segment illumination light source (not shown) for illuminating an anterior eye segment of the tested eye E and an anterior eye segment observation camera Ca1. Between the anterior eye segment of the tested eye E and the anterior eye segment observation camera Ca1, there exist the object lens Ob, a half mirror M1, wavelength selection mirrors M2, M3, and a total reflection mirror M4.

The anterior eye segment illumination source has wavelength $\lambda=700$ nm that is used as an anterior eye segment illumination light. The half mirror M1 reflects half of the light beams of wavelength 700 nm and transmits half of the light beams, respectively. The wavelength selection mirror M2 transmits all of the light beams from $\lambda=700$ nm to 770 nm, and reflects the light beams from $\lambda=500$ nm to 700 nm and from $\lambda=800$ nm to 1100 nm. The wavelength selection mirror M3 transmits half of the light beams of wavelength $\lambda=770$ nm and reflects half of the light beams, and transmits all of the light beams $\lambda=700$ nm.

The anterior eye segment illumination light beams are reflected at the anterior eye segment of the tested eye E, focused by the object lens Ob, and led to the half mirror M1. Then, the anterior eye segment illumination light beams are deflected toward the wave selection mirror M2 by the half mirror M1, transmit through the wave selection mirrors M2 and M3, and are led to the total reflection mirror M4. Moreover, the anterior eye segment illumination light beams are led to the anterior eye segment observation camera Ca1 by the total reflection mirror M4, in which an anterior eye segment image of the tested eye E is formed.

While an observer or photographer observes, on a monitor, the anterior eye segment image focused in the anterior eye segment observation camera Ca1, he moves the opthalmologic apparatus by a manual operation to perform an alignment of the apparatus itself with respect to the tested eye E.

(Alignment Detection System 6)

The alignment detection system 6 includes an X-Y alignment detection light source Os1, an alignment mirror M5, an X-Y alignment sensor Se1, a Z alignment detection light source Os2, and a Z alignment sensor Se2.

Between the half mirror M1 and the alignment mirror M5, there exists a mirror M6 having a hole h0 therein. The alignment mirror M5 totally reflects the light beam of wavelength $\lambda=700$ nm, and totally transmits the light beams below wavelength $\lambda=700$ nm and over wavelength $\lambda=800$ nm.

LED's of wavelength)=770 nm are used hereby as the X-Y alignment detection light source Os1 and the Z alignment detection light source Os2. PSD's (semiconductor position detector) are used as the X-Y alignment sensor Se1 and the Z alignment sensor Se2.

A X-Y alignment detection light beam from the X-Y alignment detection light source Os1 is reflected by the alignment mirror M5 to pass through the hole h0 of hole-made mirror M6. Then, the X-Y alignment detection light beam proceeds to the half mirror M1 and the object lens Ob to be led to a cornea C of the tested eye as a parallel light flux. A bright spot image (false image) is formed on the cornea C by the cornea reflection of the X-Y alignment detection light beam.

The X-Y alignment detection light beam reflected by the cornea C is half reflected by the half mirror M1 to reach the wavelength selection mirror M2. Then, the X-Y alignment detection light beam totally transmits the wavelength selection mirror M2 to be led to the wave selection mirror M3, which reflects a part of the X-Y alignment detection light beam to the X-Y alignment sensor Se1 and transmits the rest to the total reflection mirror M4.

The X-Y alignment sensor Se1 detects a positional difference in the X-Y direction with respect to the apparatus itself in a plane vertical to an optical axis 01 of the object lens Ob of the anterior eye segment of the tested eye E, based on the position of the bright spot image formed on the cornea C of the tested eye E, where the X direction is defined as the left and right direction and Y direction is defined as the upward and downward direction with respect to the tested eye E.

The Z alignment detection light beam from the Z alignment detection light source Os2 is projected to the cornea C of the tested eye E from a diagonal direction. A bright spot image (virtual image) is formed on the cornea C owing to cornea reflection of the Z alignment detection light beam. The Z alignment detection light beam is reflected in the diagonal direction by the cornea C to arrive at the Z alignment sensor Se2. The Z alignment sensor Se2 detects a positional difference (in the optical axis direction of the object lens Ob) in the Z axis direction with respect to the apparatus itself of the tested eye E, based on the position of the bright spot image formed on the cornea C.

The alignment detection system 6 is used to automatically perform a precise alignment of the apparatus itself with respect to the tested eye E after a rough alignment of the apparatus itself with respect to the tested eye E is completed according to the anterior eye segment observation system 5.

Since the principle of alignment for the alignment detection system 6 is publicly well-known, the detailed explanation of the principle is omitted.

(Low Magnification Ocular Fundus Photographing System 1)

The low magnification ocular fundus photographing system 1 includes a low magnification photographing illumination light source (for example, a halogen lamp) Os3, a wavelength selection mirror M7, a low magnification photographing diopter compensation lens L1, a wave selection mirror M8, a total reflection mirror M9, and a low magnification photographing camera (mono-chrome camera) Ca2.

The low magnification photographing diopter compensation lens L1, moved backward and forward along the optical axis O1, is used for compensating a refractive error of an eyeball.

The wavelength selection mirror (dichroic mirror) M7 wholly transmits the light beam over wavelength λ=800 nm, and totally reflects the light beam between λ=500 nm and 700 nm. The wavelength selection mirror M7 is also used for a high magnification photographing illumination light source Os4. The wavelength selection mirror M8 totally reflects the light beam below wavelength λ=800 nm and wholly transmits the light beam over wavelength λ=800 nm.

Light of infrared component above wavelength λ=860 nm is used as a low magnification photographing illumination light beam. The light beam of the infrared component wholly transmits through the wavelength selection mirror M7 to reach the hole-made mirror M6, by which the light beam is reflected to the half mirror M1. Moreover, the light beam, after transmitting the half mirror M1, is condensed by the object lens Ob to be led to the ocular fundus Ef of the tested eye E as an annular illumination light flux, in which the ocular fundus Ef of the tested eye E is illuminated.

The illumination light beam reflected by the ocular fundus Ef is converged by the object lens Ob to pass through the half mirror M1 and the hole h0 of the hold-made mirror M6. Then, the illumination light beam is led to the low magnification photographing diopter compensation lens L1 by way of the alignment mirror M5. After the refractive error of the eyeball is compensated by the low magnification photographing diopter compensation lens L1, the illumination light beam is led to the total reflection mirror M9 through the wave selection mirror M8. After this, the illumination light beam is deflected to the low magnification photographing camera Ca2 by the total reflection mirror M9, by which an image of the low magnified ocular fundus is focused in the low magnification photographing camera Ca2.

The low magnification ocular fundus photographing system 1, which is an optical system that corresponds to a conventional ocular fundus camera, is used for observing the ocular fundus Ef in a wide visual field and for determining a photographing position when photographing the ocular fundus at high magnification.

(Fixation Target Projection System 7)

The fixation target projection system 7 includes a fixation light source Os5 and the wavelength selection mirror M8. The fixation light source Os5 is an LED that emits light of wavelength λ=560 nm. The fixation target light from the fixation light source Os5 is deflected to the low magnification photographing diopter compensation lens L1 by the wavelength selection mirror M8 to be led to the object lens Ob through the low magnification photographing diopter compensation lens L1, the alignment mirror M5, the hole ho of the hole-made mirror M6, and the half mirror M1. The object lens Ob forms a light source image of the fixation target on the ocular fundus Ef. The examinee pays close attention to the fixation light. The gaze direction of the examined eye E is determined by the fixation target projection system 7.

The fixation light source Os5 is movably constructed in a plane perpendicular to the optical axis O2. Changing the gaze direction or the examined eye E by moving the fixation light source Os5 enables the low magnification ocular fundus photographing system 1 and the high magnification ocular fundus photographing system 2 to observe a predetermined position of the ocular fundus.

(Wave Front Aberration Compensation System 8)

The wave front aberration compensation system 8 (compensation optical system) includes a projection system and a light receiving system.

The projection system includes a wave front sensor light source Os6, a half mirror M10, a total reflection mirror M11, a wavelength selection mirror 12, a wave front compensation element (for example, a deformable mirror) M12', an astigmatism compensation variable cross-cylinder Vcc, a wavelength selection mirror M13, a Y direction tracking mirror YTM1, an X direction tracking mirror XTM1, a wavelength selection mirror M14, a total reflection mirror M15, a wavelength selection mirror M16, and a high magnification photographing diopter compensation mirror M17. An optical element of one portion of the wave front aberration compensation system 8 is positioned in an optical path of the high magnification ocular fundus photographing system 2 to be used with an optical element of the high magnification ocular fundus photographing system 2.

The wave front sensor light source Os6 is used to project a light beam of wavelength λ=830 nm to the ocular fundus Ef of the tested eye E. The half mirror M10 has the characteristics of half transmittance and half reflection. The wavelength selection mirror M12 totally transmits light above wavelength λ=800 nm, and totally reflects light below wavelength λ=800 nm.

The astigmatism compensation variable cross-cylinder Vcc plays a role of compensating a spherical power, a cylindrical power, and an axis angle. The wavelength selection mirror M13 totally transmits light above wavelength λ=860 nm, and totally reflects light below wavelength λ=860 nm.

The wavelength selection mirror M14 totally transmits light above wavelength λ=860 nm, and totally reflects light below wavelength λ=860 nm. The wavelength selection mirror M16 totally transmits light above wavelength λ=860 nm, and totally reflects light below wavelength λ=860 nm, too.

A light beam of wavelength λ=830 am emitted from the wave front sensor light source Os6 is reflected by the half mirror M10 to reach the total reflection mirror M11, which, in turn, reflects the light beam to the wavelength selection mirror M12. After transmitting through the wavelength selection mirror M12, the light beam of wavelength λ=830=nm reaches the wavelength selection mirror M13 via the wave front compensation element M12' and the astigmatism compensation variable cross-cylinder Vcc.

The light beam of wavelength λ=830 nm is reflected by the wavelength selection mirror M13 to arrive at the wavelength selection mirror M14 by way of the Y direction tracking mirror YTM1 and the X direction tracking mirror XTM1. Furthermore, the light beam of wavelength λ=830 nm is reflected by the wavelength selection mirror M14 to hit against the total reflection mirror M15, which sends out the light beam to the wavelength selection mirror M16.

The light beam of wavelength λ=830 nm is totally reflected by the wavelength selection mirror M16 to reach the object lens Ob through the high magnification photographing diopter compensation mirror M17, the wavelength selection mirror M2, and the half mirror M1. The object lens Ob projects a point light source image to the ocular fundus Ef of the tested eye E.

The light receiving system includes the half mirror M10, the total reflection mirror M11, the wavelength selection mirror M12, the wave front compensation element (deformable mirror) M12', the astigmatism compensation variable cross-cylinder Vcc, the wavelength selection mirror M13, the Y direction tracking mirror YTM1, the X direction tracking mirror XTM1, the wavelength selection mirror M14, the total reflection mirror M15, the wavelength selection mirror M16, a high magnification photographing diopter compensation mirror M17, a wave front sensor Se3 that comprises a part of the aberration measurement part which measures the optical aberration of the tested eye.

The wave front sensor Se3 includes a Hartmann's diaphragm having an aperture with numerous holes and a light receiver part for detecting a position reached by each beam that has transmitted through the numerous holes. The wave front aberration is detected based on the reached position by the beam on the light receiver of the wave front sensor Se3. The wave front sensor Se3 is publicly known.

The reflective light beam from the ocular fundus Ef takes a reverse light path, that is, the reflective light beam passes through the object lens Ob, the half mirror M1, the wavelength selection mirror M2, the high magnification photographing diopter compensation mirror M17, the wavelength selection mirror M16, the total reflection mirror M15, the wavelength selection mirror M14, the X direction tracking mirror XTM1, the Y direction tracking mirror YTM1, the wavelength selection mirror M13, the astigmatism compensation variable cross-cylinder Vcc, the wave front compensation element M12', the wavelength selection mirror M12, and the total reflection mirror M11 to reach the half mirror M10, transmitting through which the reflective light beam is led to the wave front sensor Se3.

The wave front aberration includes aberration caused by the tested eye E. Based on the aberration quantity measured by the wave front sensor Se3, the wave front compensation element M12' is controlled. The shape of the reflective surface of which is changed thereby so that the compensation of wave front aberration is performed and the optical aberration of the tested eye E is compensated thereof. The wave front compensation element M12' functions as the aberration compensation measure to compensate the aberration of the tested eye based on the signals from the aberration measurement part.

For example, the opthalmologic apparatus in the prior art can take a picture of a cell about 5 μm in size. On the other hand, the opthalmologic apparatus in accordance with the present invention can photograph a cell about 2 μm in size.

Since there is a limit in compensation quantity of the wave front aberration the wave front compensation element M12' can perform, the high magnification photographing diopter compensation mirror (optical path shift measure) M17 is moved in the direction of an arrow F-F to adjust an optical path from the wave front sensor Se3 to the ocular fundus Ef of the tested eye. This compensates most of the component of the spherical power (components of hyperopia and myopia) of refractive error of the tested eye E. Rotational adjustment of a relative angle of a pair of cylindrical lens constituting the astigmatism compensation variable cross-cylinder Vcc and an overall angle compensates most of the astigmatism component of refractive error of the tested eye E. Because of these, high-degree aberration of aberration caused by refractive error of an eye ball cannot be removed by the high magnification photographing diopter compensation mirror M17 and the astigmatism compensation variable cross-cylinder Vcc. However, the high-degree aberration can be compensated by the wave front compensation element M12'. The wave front aberration compensation system 8 can eliminate all types of aberration except for color aberration and distortion aberration to produce a clear image even at higher magnification.

The X direction tracking mirror XTM1 and the Y direction tracking mirror YTM1 constitute a part of the ocular fundus tracking control driver 9.

(High Magnification Ocular Fundus Photographing System 2)

The high magnification ocular fundus photographing system 2 is composed of an illumination system and an image receiving system. The illumination system includes the high magnification photographing illumination light source Os4 and the wavelength selection mirror M7.

The optical path of the image receiving system includes the above described wave front aberration compensation system 8 and the ocular fundus tracking control driver 9. The image receiving system includes a high magnification photographing camera Ca3 as a photographing device, an image forming lens L2, the wavelength selection mirror M12, the wave front compensation element (deformable mirror) M12', the astigmatism compensation variable cross-cylinder Vcc, the wavelength selection mirror M13, the Y direction tracking mirror YTM1, the X direction tracking mirror XTM1, the wavelength selection mirror M14, the total reflection mirror M15, the wavelength selection mirror M16, and the high magnification photographing diopter compensation mirror M17. A color CCD camera is used as the high magnification photographing camera Ca3.

A xenon lamp, for example, is used as the high magnification photographing illumination light source Os4. Light of wavelength $\lambda$=500 nm to 700 nm from the xenon lamp is used as the high magnification photographing illumination beam. The illumination beam of wavelength $\lambda$=500 nm to 700 nm from the xenon lamp is totally reflected by the wavelength selection mirror M7 to reach the hole-made mirror M6, by which the illumination beam is deflected. Then, the deflected illumination beam hits against the ocular fundus Ef of the tested eye E as an annular light beam, by way of the half mirror M1 and the object lens Ob.

The reflected illumination beam from the ocular fundus Ef is converged by the object lens Ob and reflected to the wavelength selection mirror M2 via the half mirror M1. The illumination beam, which reached the wavelength selection mirror M2, proceeds to the high magnification photographing diopter compensation mirror M17, the wavelength selection mirror M16, the total reflection mirror M15, the wave length selection mirror M14, the X direction tracking mirror XTM1, the Y direction tracking mirror YTM1, the wavelength selection mirror M13, the astigmatism compensation variable cross-cylinder Vcc, the wave front compensation element M12', and the wavelength selection mirror M12. Moreover, the illumination light is totally reflected by the wavelength selection mirror M12 to be led to the image forming lens L2, which enables magnification conversion by an electrically movable revolver. The illumination light reflected at the ocular fundus Ef is focused on a photographing surface of the high magnification photographing camera Ca3 through the image forming lens L2.

(Ocular Fundus Tracking Control Driver 9)

The ocular fundus tracking control driver 9, which shares a part thereof with a tracking detector 10, is adjusted to dispose a photographic visual field of the high magnification ocular fundus photographing system 2 at a predetermined position of the ocular fundus Ef so that a gaze direction of the tested eye E is detected to follow a photographic direction of the high magnification ocular fundus photographing system 2 to the gaze direction of the tested eye E.

The use of the ocular fundus tracking control driver 9 enables a permanently still image of the ocular fundus to be formed on the high magnification photographing camera Ca3 without the influence of a fixation micro-movement of the tested eye E. As a result, a clear image of the ocular fundus without a blur can be obtained even in a case where an observation or photographing at the level of a visual cell with optical resolution function is needed.

The tracking detector 10 includes a visual line detection light source Os7, a half mirror 18, an X direction scanning mirror XTM2, a Y direction scanning mirror YTM2, a visual line detection optical axis offset mirror M19, a pinhole plate Pi, and a visual line (direction) detection sensor (light receiving element) Se4.

The pinhole plate Pi is provided in front of the visual line detection sensor Se4. An LED that emits near infrared of wavelength $\lambda=945$ nm is used as the visual line detection light source Os7. The near infrared is not used for taking a picture.

Light of the near infrared from the visual line detection light source Os7 is deflected by the half mirror 18 to the Y direction scanning mirror YTM2 and then to the X direction scanning mirror XTM2, by which the light of the near infrared is deflected to the wavelength selection mirror M13.

After the light of the near infrared of $\lambda=945$ nm totally transmits the wavelength selection mirror M13, it proceeds to the wavelength selection mirror M14 via the Y direction tracking mirror YTM1 and the X direction tracking mirror XTM1.

After the light of the near infrared of $\lambda=945$ nm transmits through the wavelength selection mirror M14, it goes to the visual line detection optical axis offset mirror M19, by which the light of the near infrared is deflected to the wavelength selection mirror M16. After passing through the wavelength selection mirror M16, the light of the near infrared is projected out to the ocular fundus Ef of the tested eye E by way of high magnification photographing diopter compensation mirror M17, the wavelength selection mirror M2, the half mirror M1, and the object lens Ob.

A beam from the visual line detection light source Os7 should illuminate a wide range of predetermined positions on the ocular fundus Ef. That is, an area of the ocular fundus Ef to be illuminated should be a size sufficient to cover the scanning light receiving area of the visual line detection sensor Se4.

A wide range of areas can be uniformly illuminated by using an optical structure for the ocular fundus illumination system that is used for a general ocular fundus camera.

The pinhole plate Pi is placed at a conjugate position of the ocular fundus Ef. A photo diode, for example, is used as the visual line direction detection sensor Se4. The wavelength selection mirror M16 is used to separate a photographing optical path of the high magnification ocular fundus photographing system 2 from a detection optical path of a gaze direction detection axis.

As an example of the visual line direction detection sensor Se4, an APD (Avalanche Photo Diode) except for a photo diode (including a PIN photo diode), or photomultiplier, each having high sensitivity, can be used dependent upon the need.

The visual line detection optical axis offset mirror M19 is used to move the gaze direction detection axis, and is disposed out of the photographing optical path of the ocular fundus and within an optical path of the tracking detector 10 for the visual line direction detection.

That is, if the visual line detection optical axis offset mirror M19 is slanted in the two dimensions (X and Y direction), a position on the ocular fundus as a tracking target is arbitrarily selected.

In accordance with the wavelength selection mirrors M14 and M16, the visual line detection optical axis offset mirror M19 bends only near infrared of wavelength $\lambda=945$ nm to move the detection axis of the gaze direction. This does not produce any influence on the photographing optical axis with respect to the ocular fundus.

The X direction scanning mirror XTM2 and the Y direction scanning mirror YTM2 play a function of scanning a pinhole corresponding region (reflective region) on the ocular fundus that is conjugate to a pinhole on the pinhole plate Pi. The pinhole corresponding region is moved so that the scanning draws, for example, an oval locus on the ocular fundus. The idea of oval connotes a circle. The pinhole corresponding region (reflective region) is a visual field for the visual line direction detection.

For example, when vibration directions of the X direction scanning mirror XTM2 and the Y direction scanning mirror YTM2 are orthogonal to each other in the vibration direction and the two mirrors are vibrated at the same frequency and amplitude with a 90-degree phase difference, a circular scanning can be carried out.

The tracking target for the visual field of the visual line direction detection may be approximately circular. Typical of the tracking target are an optic disc FNP shown in FIG. 3, a macula fovea, an intersection of blood vessels, a white spot on the ocular fundus and a drusen.

Figure 3:
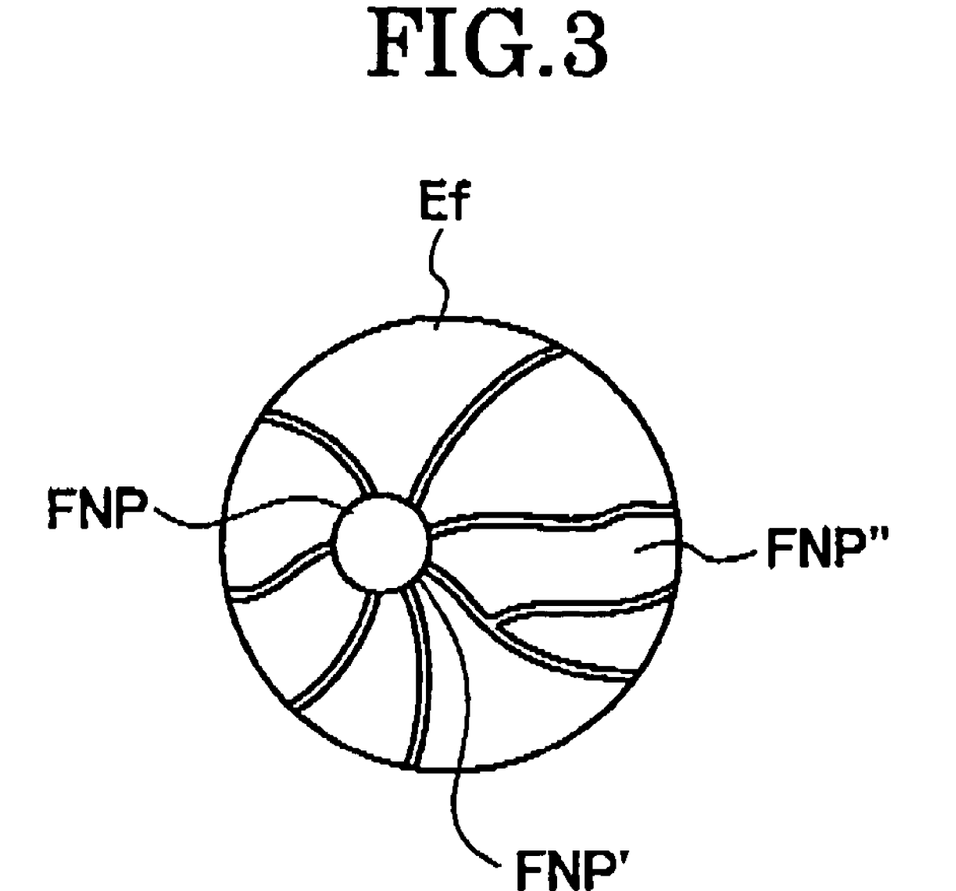
FIG. 3 is an illustrative view of an ocular fundus of a tested eye in FIG. 1.

One of photographing targets is a cell in the ocular fundus. When the cell (on order of micron) in the ocular fundus is photographed as a photographing target, an optic disc FNP (on order of millimeter) may be selected as a tracking target.

Figure 4A:
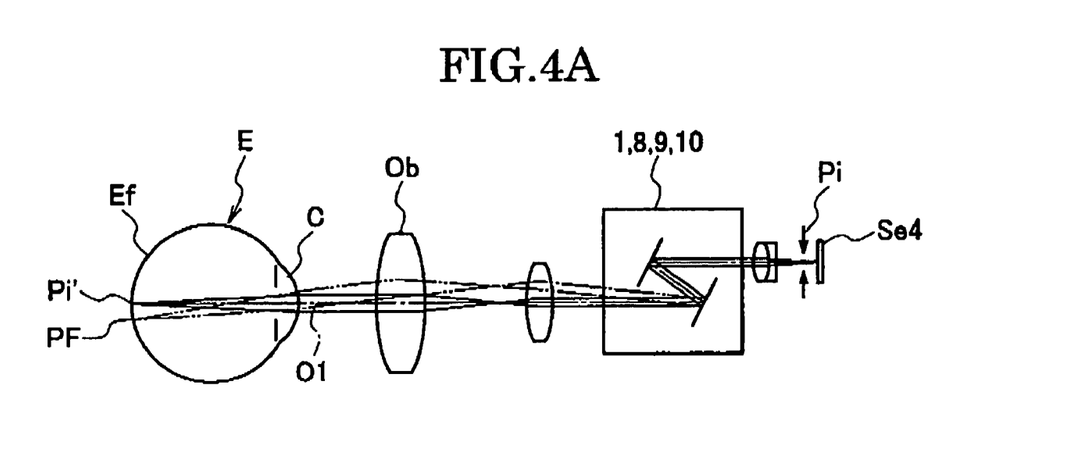
FIG. 4A is an illustrative view of an optical path showing an offset for an ocular fundus photographing beam and a detection beam, where tracking control is explained for the ocular fundus of the tested eye shown in FIG. 1.

As shown by the solid lines in FIG. 4A, light of wavelength $\lambda=945$ nm from a pinhole corresponding area Pi' on the ocular fundus Ef proceeds to the pinhole plate Pi by way of the object lens Ob, the half mirror M1, the wavelength selection mirror M2, the high magnification photographing diopter compensation mirror M17, the wavelength selection mirror M16, the visual line detection optical axis offset mirror M19, the X direction tracking mirror XTM1, the Y direction tracking mirror YTM1, the wavelength selection mirror M13, the X direction scanning mirror XTM2, the Y direction scanning mirror YTM2, and the half mirror M18. The light that has passed through the pinhole of the pinhole plate Pi is received by the visual line detection sensor Se4.

PF represents a tracking target when a cell is examined. For example, as a tracking target, the optic disc FNP can be selected.

The scanning is carried out to move along an edge FNP' of the optic disc FNP as a tracking target. The adjustment of moving along the edge FNP' is made based on an adjustment of a tilt of the visual line detection optical axis offset mirror M19.

Figure 4B:
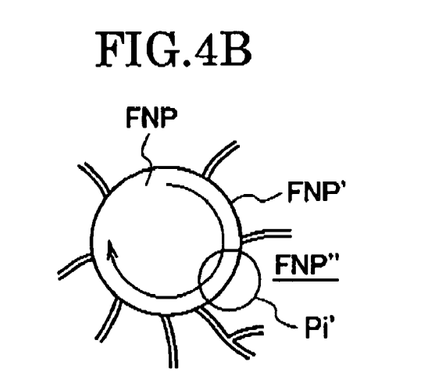
FIG. 4B is an illustrative view of a locked state in which a tracking target is locked owing to tracking by using a pinhole corresponding region.

As shown in FIG. 4B, the tracking target is the optic disc FNP. The tracking target is brighter than the ocular fundus area FNP'''. When the edge FNP' of optic disc FNP is identical to a circular arc locus drawn by the pinhole corresponding region Pi', an output from the visual line detection sensor Se4 does not change in the course of scanning.

Figure 4C:
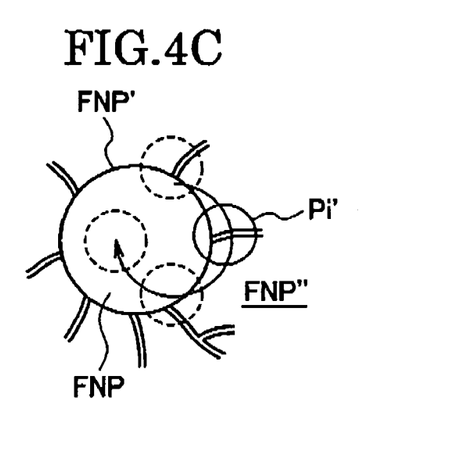
FIG. 4C is an illustrative view of a state in which the tracking target to be detected by the pinhole corresponding region is shifted to the right.

On the contrary to FIG. 4B, as shown in FIG. 4C, the circular arc locus drawn by the pinhole corresponding region Pi' is shifted to the right with respect to the optic disc FNP. An average output for one period of the output from the visual line detection sensor Se4 has no variation because most of the pinhole corresponding region Pi' overlaps the optic disc FNP. However, the output of the visual line detection sensor Se4 when the pinhole corresponding region Pi' is in the right is different from that when the pinhole corresponding region Pi' is in the left.

Figure 4D:
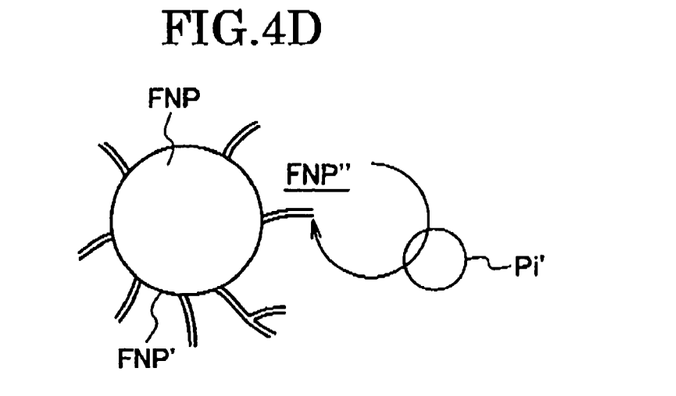
FIG. 4D is an illustrative view of a state in which the tracking target to be detected by the pinhole corresponding region is unlocked.

As shown in FIG. 4D, the locus drawn by the pinhole corresponding region Pi' is away from the optic disc FNP and in the ocular fundus region FNP'". The average output for one cycle of the visual line detection sensor Se4 when the locus is in the ocular fundus region FNP'" is lower than that when the edge FNP' is identical to a circular locus drawn by the pinhole corresponding region Pi'.

The output of the visual line detection sensor Se4 is applied to a process circuit that will be discussed. The process circuit adjusts the X direction tracking mirror XTM1 and the Y direction tracking mirror YTM1 so that for example, the average outputs are equal in the up and down and left and right directions.

According to this, as shown in FIG. 4B, the optic disc FNP, a tracking target, is locked, which executes tracking with respect to the ocular fundus Ef. When, for example, tracking is performed in the left and right directions, the process circuit drives the X direction tracking mirror XTM1 and the Y direction tracking mirror YTM1 for tracking adjustment to the ocular fundus Ef, in order that with respect to an amplitude center of a fixation micro-movement for the ocular fundus Ef, an average output from the visual line direction detection sensor Se4 obtained by scanning the left half is equal to that obtained by scanning the right half.

An explanation has been made so far regarding the optic disc FNP as a tracking target. When the tracking target is darker than the ocular fundus region FNP'" like a macula fovea, tracking process may be performed by treating as a reference an average output of the darker region. Namely, the tracking target should be distinguished between a specific area and the rest of it in terms of brightness.

An explanation is given assuming that the scanning locus regarding the tracking target is elliptic. However, the scanning locus is not limited to this, and may be square or triangular.

In this way, the gaze direction for the tested eye E is detected, according to the output from the visual line direction detection sensor Se4 that responds to the scanning locus drawn by the pinhole corresponding region Pi' on the ocular fundus Ef. Controlling the X direction tracking mirror XTM1 and the Y direction tracking mirror YTM1 based on the detection result enables a photographing position for the high magnification ocular fundus photographing to follow the fixation micro-movement.

In other words, a small-sized specific position should be determined as a photographing target, and a specific object adjacent to the photographing target should be selected as a tracking target. In the case, when the photographing target is small-sized, the optical system for the eye of human beings cannot be regarded as perfect, and instead should be handled as imperfect. Owing to this, a wave front compensation element M12' should be inserted in the optical path.

Under the structure, when a cell is selected as the photographing target, it is possible to know a condition of the cell, for example, the condition that the cell is now sick or will be sick.

An explanation is made in which the wavelength of light in the tracking detector 10 is different from that of the illumination light for the low magnification ocular fundus photography. The reflective light derived from the illumination light of the ocular fundus for the low magnification ocular fundus photography may be used in a constitution to detect the gaze direction. In the case, the visual line detection light source Os7 should not be provided as an exclusive light source.

Since the optical path of the high magnification ocular fundus photographing system 2 includes the same X direction tracking mirror XTM1 and Y direction tracking mirror YTM1, a photographing range follows a fixation micro-movement of the eyeball and is always fixed at a predetermined position.

Because the tracking detector 10 offsets a visual line detection beam shown by the solid lines and a reflective beam from the photographing portion PF shown by the dotted lines in FIG. 4A, a desired photographing portion PF on the ocular fundus can be photographed.

(Operation Procedures)

An examiner selects a photographing magnification of the high magnification ocular fundus photographing system 2 in accordance with a purpose. At the same time, based on the beforehand measurement information of the tested eye E, the examiner sets astigmatism compensation quantity and compensation direction at the astigmatism compensation variable cross-cylinder Vcc.

The face of an examinee should be placed on a chin rest (not shown) of the apparatus, and his forehead should be put at a forehead receiver, in order to fix the face of the examinee. The eye E to be tested is determined as to where the eye is disposed with respect to the apparatus.

An examiner observes an anterior eye segment through the anterior eye segment observation system 5 by pulling the apparatus itself towards the near side, and matches a pupil of the tested eye E with the optical axis 01 of the apparatus regarding their positions by a manual operation. Then, the apparatus itself is moved along the optical axis 01 to the examinee's side. According to the manual adjustment, when a position of the tested eye E is within a range of predetermined alignment, the alignment detection system 6 automatically operates to perform an alignment of the apparatus itself with respect to the tested eye E.

The optical axis 01 of the apparatus itself is precisely aligned with respect to the tested eye E, the examinee can inspect the fixation light source Os5 within the apparatus itself. Examinee's close observation of the fixation light source Os5 fixes a gaze direction of the tested eye E.

The examiner operates the low magnification photographing diopter compensation lens L1 to focus on the ocular fundus Ef. The high magnification photographing diopter compensation mirror M17 is moved in association with the low magnification photographing diopter compensation lens L1 to be shifted to the approximately focused position.

Figure 5:
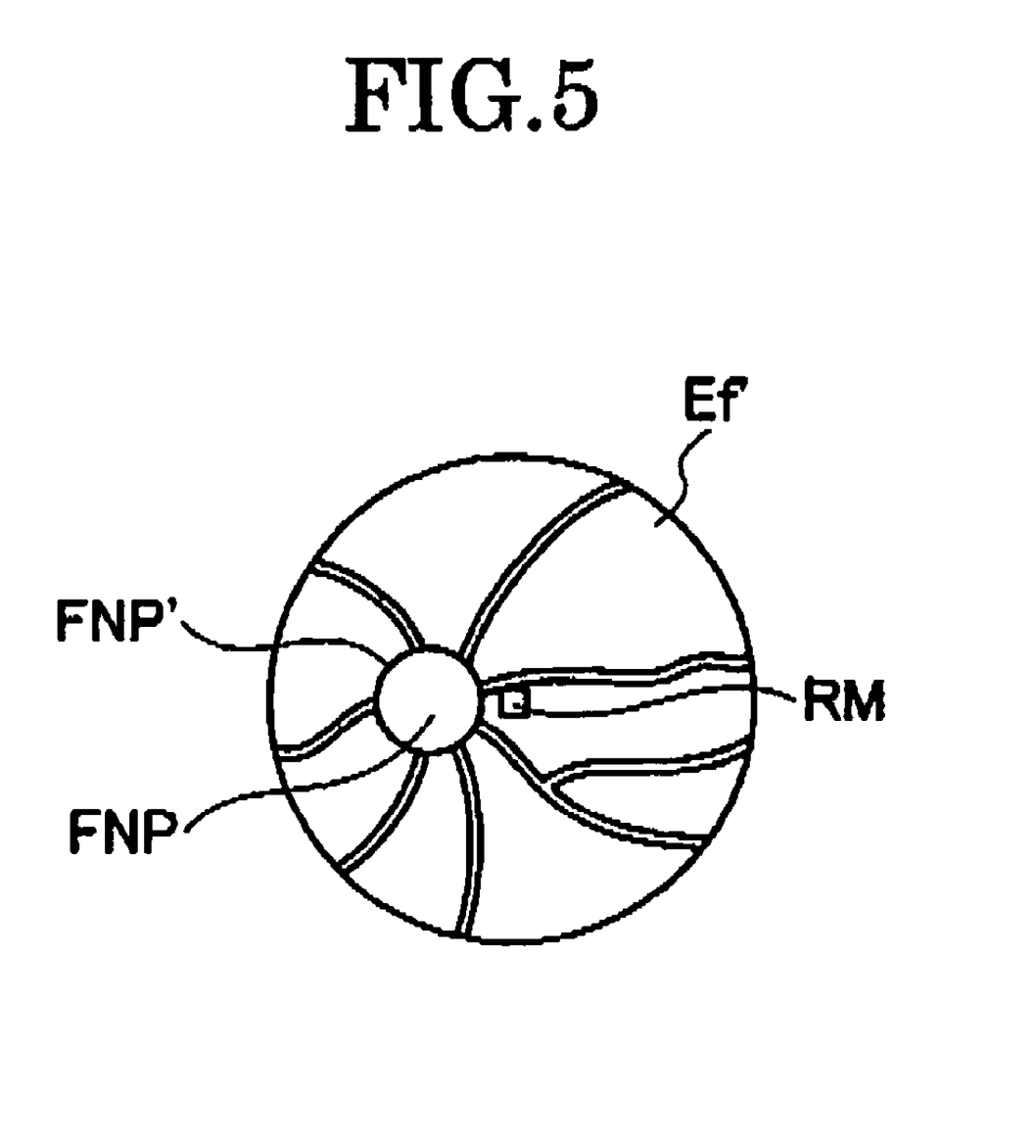
FIG. 5 is an illustrated view illustrating the ocular fundus photographing image of a tested eye as shown in FIG. 1.

The examiner observes an ocular fundus image Ef' of a monitor screen of the low magnification ocular fundus photographing system 1. As shown in FIG. 5, a square mark RM, which represents a photographing position to be photographed by the high magnification ocular fundus photographing system 2, is displayed in the ocular fundus image Ef' observed by the low magnification ocular fundus photographing system 1. The examiner can confirm the photographing position the high magnification ocular fundus photographing system 2 takes a picture of, by inspecting the square mark RM.

When the photographing position the high magnification ocular fundus photographing system 2 photographs is not a desired position, the examiner moves the fixation light source Os5 to shift the gaze direction of the examinee. This enables a desired photographing position to be at the square mark RM. In this case, since a positional relationship between a position of a cornea reflective image and a pupil of the tested eye E varies according to a shift of the gaze direction, the alignment optical system 6 compensates this. When the ocular fundus image observed by the low magnification photographing system 1 is stored by a storing device (not shown), it can be later confirmed where on the ocular fundus Ef the photographing position, which the high magnification ocular fundus photographing system 2 has photographed, belongs to.

A projection area of a beam from the visual line detection light source Os7 of the tracking detector 10 can be observed, by using the low magnification ocular fundus photographing system 1.

When the visual line detection optical axis offset mirror M19 is adjusted, slanted in two-degree dimensions, a tracking position of the ocular fundus Ef can be offset at a desired position.

An offset adjustment is made, by observing a projection position of a beam from the visual line detection light source Os7. When a movement position of the visual line detection light axis decided by a tilt angle of the visual line detection optical axis offset mirror M19 is overlapped with the ocular fundus image Ef' to be displayed, an offset adjustment based on the display can be performed. By analyzing the ocular fundus image Ef', a slant angle of the visual line detection optical axis offset mirror M19 may be adjusted and controlled so that a visual line detection optical axis matches with a desired position of the optic disc FNP.

After setting a photographing position and a tracking target position by the high magnification ocular fundus photographing system 2, the opthalmologic apparatus performs the compensation by the wave front aberration compensation system 8 and the ocular fundus tracking control using a control switch (not shown) of the high magnification ocular fundus photographing system 2.

The high magnification ocular fundus photographing system 2 can obtain a clear image at the level of a visual cell in which high-degree aberration of the tested eye E is compensated, according to the aberration compensation of the wave front compensation system 8. In addition, tracking control of the ocular fundus Ef can provide an ocular fundus image at the level of a visual cell without a blur in spite of a fixation micro-movement.

With regard to diopter compensation of the high magnification ocular fundus photographing system 2, the examiner may provide a setting device that adjusts a small amount of offset concerning the focused surface automatically followed by a diopter compensation apparatus (not shown). The setting device for the offset adjustment is used to set which portion of the ocular fundus structure should be photographed in the deep direction regarding the depth of field of the high magnification ocular fundus photographing system 2.

When the examiner pushes a photographing switch, the control circuit observes the state of each optical system. If, for example, an extraordinary event such as "off tracking" has not occurred, the examiner emits the high magnification photographing illumination light source Os4 to take a picture by using the high magnification ocular fundus photographing system 2.

Photographed data is, for example, recorded in a film or filed as an electronic image. At the same time, the following are also recorded: which is photographed, left or right eye; diopter of left and right eyes; the astigmatism compensation variable cross-cylinder Vcc; the wave front compensation element M12'; photographing magnification; offset quantity of the tracking target and photographing position; and images of the low magnification ocular fundus photographing system 1.

In order to compensate a focal depth of the high magnification ocular fundus photographing system 2, which is very shallow, as an additional function, by a trigger based on a one-time photographic switch operation or by triggers based on plural-time photographic switch operations, an image is taken that is derived by shifting backward and forward the focus for the high magnification photographing, at a step of the degree of the focal depth of the high magnification ocular fundus photographing system 2.

The so-called focus bracketing photographing can provide a clear ocular fundus image, even in photographing the ocular fundus image Ef' having ruggedness.

The following measure can be thought of in order to obtain a clear ocular fundus image of each tissue in the depth direction of the ocular fundus Ef.

The imaging forming lens L2 is used as a focusing device for substantially focusing corresponding to the refractive power of the tested eye by moving a part of the optical system comprising the photographing system along the optical axis direction. After substantially focusing to the ocular fundus Ef of the tested eye E by moving the imaging forming lens L2 in the optical axis direction by means of a moving device (not shown), the imaging forming lens L2 is sequentially adjusted to move stepwise at a predetermined minute pitch centering on the focused position of the image forming lens L2, and thereby, the ocular fundus image of the tested eye E is photographed at each of the positions in which the imaging forming lens L2 is sequentially adjusted to move stepwisely.

Instead of using the image forming lens L2 as the focusing device, the high magnification photographing compensation mirror M17 as the optical path length conversion device is used as the focusing device. After substantially focusing to the ocular fundus Ef of the tested eye E by moving the imaging forming lens L2 in the optical axis direction by means of a moving device (not shown), the high magnification photographing compensation mirror M17 is sequentially adjusted to move stepwisely at a predetermined minute pitch centering on the focused position of the high magnification photographing compensation mirror M17, and thereby, the ocular fundus image of the tested eye E is photographed at each of the positions in which the image forming lens L2 is sequentially adjusted to move stepwisely.

Moreover, these focusing devices can be used as a first focusing device, and as a second focusing device, a movable lens L3 which is moved in the optical axis direction by a piezo element PeZ can be disposed between the astigmatism compensation variable cross-cylinder Vcc and the wave front compensation element M12'. In this case, the movable lens L3 is sequentially adjusted to move stepwisely at a predetermined minute pitch centering on the position corresponding to the focused position of the first focusing device, and thereby, the ocular fundus image of the tested eye E is photographed at each of the positions in which the movable lens L3 is sequentially adjusted to move stepwisely. The movable lens L3 is driven at a high speed by means of the piezo element PeZ. The movable lens L3 is used for tracking at a high speed the deformation of the wave front compensation element M12'.

That is, if the wave front compensation element M12' is deformed according to the measurement result of the wave front sensor Se3, spherical aberration based on the deformation is newly generated. The movable lens L3 is used to remove the newly generated spherical aberration.

According to the present invention, the opthalmologic apparatus capable of obtaining a plurality of images of the ocular fundus with different focused positions in the depth direction of the ocular fundus and also a clear image of the ocular fundus of each tissue in the depth direction is provided.

While preferred embodiment of the invention has been described and illustrated above, it should be understood that these are exemplary of the invention and are not to be considered as limiting. Additions, omissions, substations, and other modifications can be made without departing from the sprit or scope of the present invention. Accordingly, the invention is not to be considered as being limited by the foregoing description, and is only limited by the scope of the appended claims.

What is claimed is:

1. An ophthalmologic apparatus, comprising:
a photographing system that illuminates an ocular fundus of a tested eye, and photographs an image of the ocular fundus of the tested eye based on a reflective beam from the ocular fundus;
an aberration measurement part for measuring an optical aberration of the tested eye;
an aberration compensation device disposed in the photographing system for compensating the aberration of the tested eye based on signals from the aberration measurement part; and
a focusing device for substantially focusing corresponding to a refractive power of the tested eye by moving a part of an optical system comprising the photographing system along an optical axis direction, wherein
after performing the substantial focusing of the image of the ocular fundus by the focusing device, the focusing device is sequentially adjusted to move stepwise at a predetermined minute pitch centering on the focused position, and the image of the ocular fundus of the tested eye is photographed at each of the positions that the focusing device is sequentially adjusted to move stepwisely.

2. The ophthalmologic apparatus according to claim 1, wherein the focusing device is a movement device for moving a lens system comprising the photographing system.

3. The ophthalmologic apparatus according to claim 1, wherein the focusing device is an optical path length conversion device comprising the photographing system.

4. An ophthalmologic apparatus, comprising:
a photographing system that illuminates an ocular fundus of a tested eye, and photographs an image of the ocular fundus of the tested eye based on a reflective beam from the ocular fundus;
an aberration measurement part for measuring an optical aberration of the tested eye;
an aberration compensation device disposed in the photographing system for compensating the aberration of the tested eye based on signals from the aberration measurement part;
a first focusing device for substantially focusing corresponding to a refractive power of the tested eye by moving a part of an optical system comprising the photographing system along an optical axis direction; and
a second focusing device which, after performing the substantial focusing of the image of the ocular fundus by the first focusing device, is sequentially adjusted to move stepwisely at a predetermined minute pitch centering on the focused position, wherein
each of the images of the ocular fundus of the tested eye is photographed at each of the positions in which the second focusing device is sequentially adjusted to move stepwisely.

* * * * *